United States Patent [19]

Jizomoto

[11] Patent Number: 4,673,567

[45] Date of Patent: Jun. 16, 1987

[54] PROCESS FOR PREPARING LIPOSOME COMPOSITION

[75] Inventor: Hiroaki Jizomoto, Osaka, Japan

[73] Assignee: Shionogi & Co., Ltd., Osaka, Japan

[21] Appl. No.: 763,785

[22] Filed: Aug. 8, 1985

[30] Foreign Application Priority Data

Aug. 16, 1984 [JP] Japan ............................ 59-171265

[51] Int. Cl.⁴ .................. B01J 13/02; A61K 9/52
[52] U.S. Cl. ...................... 424/38; 264/4.3; 264/4.6
[58] Field of Search .......... 424/38; 252/316; 264/4.3, 4.6

[56] References Cited

U.S. PATENT DOCUMENTS

| | | | |
|---|---|---|---|
| 4,217,344 | 8/1980 | Vanlerberghe et al. | 424/19 |
| 4,235,871 | 11/1980 | Papahadjopoulos et al. | 264/4.6 |
| 4,298,594 | 11/1981 | Sears et al. | 424/19 |
| 4,389,330 | 6/1983 | Tice et al. | 424/32 |
| 4,483,847 | 6/1983 | Augart | 424/22 |
| 4,485,054 | 11/1984 | Mezei et al. | 264/4.6 |
| 4,515,736 | 5/1985 | Deamer | 264/4.3 |
| 4,532,089 | 7/1985 | MacDonald | 264/4.3 |
| 4,540,410 | 9/1985 | Wood et al. | 34/5 |

*Primary Examiner*—Ronald W. Griffin

[57] ABSTRACT

Novel process for liposome compositions capable to retain larger amount of drugs with a small amount of phospholipid and to provide, therefore, safer medications of various drugs, which comprises dispersing multilamella vesicles or small unilamella vesicles in an aqueous medium in the presence of one or more clinically active ingredients at or over a temperature of the gel/liquid crystal-phase transition wherein lyophilization may be made before or after the dispersion.

4 Claims, No Drawings

PROCESS FOR PREPARING LIPOSOME COMPOSITION

BACKGROUND OF THE INVENTION

1. Field of the Invention

The present invention relates to processes for preparing liposome compositions.

2. Prior Art

A process to prepare liposome compositions is disclosed in JPN Unexam. Pat. Pub. No. 53-142514 where the liposome compositions which have been formulated and phospholipid, an active ingredient, and adjuvants are lyophilized for stable storage. According to other processes disclosed in JPN Unexam. Pat. Pub. Nos. 57-82310 and 57-82311, freeze-dried liposomes are prepared with no organic solvent and are formulated into liposome compositions by the use of an aqueous medium which may or may not contain an active ingredient.

On the other hand, a process is disclosed in the JPN Unexam. Pat. Pub. No. 58-152812, wherein small unilamella vesicles (hereinafter referred to as SUV) or large unilamella vesicles (hereinafter referred to as LUV) are prepared by dispersing a special phospholipid in an aqueous medium having a specific pH-value.

SUMMARY OF THE INVENTION

This invention provides processes for preparing liposome compositions which comprises dispersing multilamella vesicles or small unilamella vesicles in an aqueous medium in the presence of one or more clinically active ingredients at or over a temperature of the gel-phase/liquid crystal-phase transition wherein lyophilization may be made before or after the dispersion.

DESCRIPTION OF THE PREFERRED EMBODIMENT

Problem

In the prior art, when freeze-dried liposome compositions are dispersed in an aqueous medium, which may or may not contain an active ingredient, the regenerated liposomes are generally in the form of multilamella vesicles (hereinafter referred to as MLV). This means that each room of regenerated liposomes (captured volume) is small and, therefore, the uptake rate of the active ingredient into the room is low. Additionally, if a freeze-dried liposome prepared from synthetic lecithin is dispersed in an aqueous medium at room temperature, even liposome is not regenerated.

The present inventor has studied with the purpose of obtaining regenerated liposomes, each of which has a large captured volume and is capable to highly entrap an active ingredient in the room, when preparing liposome compositions by dispersing freeze-dried liposomes in an aqueous medium.

Means for Resolving the Problem

In order to prepare liposome compositions by dispersing freeze-dried liposomes in an aqueous medium, it should be confirmed that liposomes can, even if the lipid of them is composed of a lecithin, be regenerated when the system is operated at an elevated temperature over the gel-/liquid crystal-phase transition temperature with regard to the lecithin involved.

Active ingredients to be entrapped may be 1 added by way of lyophilization of the liposomes, or 2 added to the freeze-dried liposomes; the resulting mixtures being employed for the completion of this invention.

Additionally, the process of the present invention can be employed in the course of dispersing freeze-dried liposomes in an aqueous medium where active ingredients are dissolved or dispersed.

Lecithins, i.e., saturated or unsaturated phosphatidyl choline, which are lipids composing liposome, are employed for this invention. These lecithins may contain phosphatidyl serine, phosphatidyl ethanolamine, phosphatidyl inositol, diphosphatidyl glycolol, phosphatidate, sphingomyelin, or the like; and further contain cholesterol or electrically charged substances (e.g., stearylamine, dicetylphosphate). Such lecithins may be derived from yolk, soybean, or tissues of the other animals or plants, hydrogenates thereof, and synthetic lecithins, which lecithins may be employed individually or in admixture of them. For instance, dipalmitoyl=phosphatidylcholine, distearoyl=phosphatidylcholine, 1-palmitoyl-2-strearoyl=phosphatidylcholine, 1-stearoyl-2-palmitoyl=phosphatidylcholine, and the like can be employed solely or in combination.

The gel-/liquid crystal-phase transition temperature of the usual lipids is listed in a disclosure of Ann. Rev. Bioeng., 9, 467 (1980). A heating operation is not, of course, required in the regeneration step of the gel-/liquid crystal-phase transition temperature is room temperature or below; this case, therefore, does not fall within the scope of this invention.

The freeze-dried liposomes employed in this invention are the freeze-dried MLV or SLV prepared by the known method, which may be obtained by means of any method for lyophilization. Examples of the active ingredients involved are anti-cancer agents such as 5-fluorouracil, neomycin, bleomycin, or the like; antibiotic agents such as cefalexin, latamoxef, or the like; enzymes or homologues such as urokinase or the like; peptides such as interferon, interleukin, globulin, insulin or the like; nucleic acids such as DNA, RNA, or the like; vitamins; or the other agents such as sulfamethoxazole, phenobarbital, or the like.

Water, brine (e.g., isotonic brine), buffer (e.g., phosphate buffer, trisaminomethane buffer) or the like is employed as an aqueous medium in which the freeze-dried liposome are dispersed; the choice depending on the purposes for which the resulting liposome composition is used. The thus-obtained liposome compositions may be orally or parenterally administered to subjects directly or in the state of a purified dispersion by removing the excessive active agent remaining outside the liposome by means of centrifugal separation, ultrafiltration, gelfiltration, or the like.

Effects

The liposome compositions prepared by the present invention, the uptake-rate into which is high, envelop the aimed active ingredient therein with high efficiency. Since each regenerated liposome has a large captured volume, a large amount of the active ingredient can be entrapped in it by a less amount of the lipid. This means that the liposome compositions can present problems, such as toxicity due to phospholipid when they are administered, or the like.

Additionally, both liposome and active ingredients can be stored in a stable state, because the active ingredient to be entrapped may be admixed at the time when the freeze-dried liposomes are regenerated.

The present invention will be explained in more detail by the following examples, which are not presented to limit the scope of this invention, but only to specifically describe the practical embodiments.

EXAMPLE 1

In chloroform was dissolved 700 mg of D,L-dipalmitoylphosphatidyl choline (DPPC) (type grade I, Sigma Chemical Co., Ltd.), then the chloroform was removed by a rotary-evaporator to form a thin layer of phospholipid on the inner wall of the round-bottom flask. The phospholipid was dried sufficiently under reduced pressure, to which 25 ml of water was added. The mixture was shaken by hand at 50° C. for about 7 minutes to give an dispersion of MLV. The dispersion was frozen by the use of dry ice/acetone and dried by vacuum lyophilization. The powder obtained was collected, 10 mg of which was then weighed and placed in each tube for centrifugal separation. A solution of 5-Fluorouracil (5-FU) (5 mg/ml) dissolved in purified water, 2- and 10-fold diluted aqueous isotonic sodium chloride solutions, and 0.02M phosphate buffer was added into the tubes in amounts of 0.4 ml each. The mixture was swelled and dispersed well, then warmed up and kept at 50° C. for five minutes and washed twice with an isotonic phosphate buffer solution (pH 7.4) at room temperature by means of ultra-centrifugal separation (85, 000 g×60 minutes). The uptake rate of 5-FU into liposome and the captured volume of liposome are listed in Table 1.

The uptake rate was calculated by the following formula:

$$\frac{\text{Amount of an active ingredient taken into liposome}}{\text{Amount of an active ingredient employed}} \times 100$$

The active ingredient taken into the liposome is released with Triton®X−100 and quantitatively analyzed by liquid chromatography.

In the case of 5-FU, the conditions of the chromatography are:

Nucleocil $_{10}C_{18}$, 0.05M potassium dihydrogenphosphate/acetatonitrile=75/25, 265 nm.

The captured volume was calculated by the following formula:

[(Volume (μl) of aqueous solution of the active ingredient employed)×(Uptake rate)]/(Weight (mg) of lipid employed)

Before this experiment, it was confirmed that 5-FU was never adsorbed on the liposome layer.

TABLE 1
Freeze-dried sample of DPPC-MLV with 5-FU

| Solvent | Ionic Strength (I) | Uptake rate (%) | Captured Vol (μl/mg) |
|---|---|---|---|
| Purified water | 0 | 41.8 | 16.6 |
| 1/10 Isotonic brine | 0.015 | 29.7 | 11.6 |
| ½ Isotonic brine | 0.077 | 3.8 | 1.5 |
| 0.02 M phosphate buffer | 0.052 | 5.2 | 1.9 |

EXAMPLE 2

Ultra-sonic wave (Daigaku ultra-sonic wave grinder, medium size tip, 120W×3 minutes) was radiated onto the MLV dispersion prepared with 300 mg of DPPC (Sigma I) in the same manner as in Example 1 to give a suspension of SUV. The SUV suspension was subject to cetrifugal separation (85,000 g×30 minutes), and then the supernatant was freeze-dried like in Example 1. Thus obtained freeze-dried sample of SUV was employed for such regeneration test as in Example 1. The results are summarized in Table 2. Referrence 5 shows the comparative test result which was obtained by merely mixing the freeze-dried liposomes with an aqueous solution of 5-FU at room temperature, without heating over the phase transition temperature concerning the membrance.

TABLE 2
Freeze-dried sample of DPPC-SUV with 5-FU

| | Solvent | Uptake rate (%) | Captured Vol. (μl/mg) |
|---|---|---|---|
| 1 | Purified water | 36.7 | 14.3 |
| 2 | 1/10 Isotonic brine | 22.4 | 8.6 |
| 3 | ½ Isotonic brine | 1.3 | 0.5 |
| 4 | 0.02 M Phosphate buffer | 1.9 | 0.7 |
| 5 | Purified water (at r.t.) | 0.1 | 0.04 |

EXAMPLE 3

To a mixture of 10 mg of freeze-dried sample of MLV obtained in Example 1 with 2 mg of crystalline 5-FU was added 0.4 ml of purified water. The suspension was swelled and dispersed well and kept at 50° C. for 5 minutes. In the same manner as in Example 1, the uptake rate into liposome was measured thereafter: the uptake rate and captured volume were 37.5% and 14.5 μl/mg, respectively.

EXAMPLE 4

Cefalexin (5 mg/ml) or latamoxef (3 mg/ml) in place of 5-FU in Example 1 was employed for the test together with a solvent of purified water, ½ isotonic brine, or 0.05M phosphate buffer solution (pH 7.4). The results are listed in Table 3. Data on liposome (MLV) enveloping latamoxef are also shown as a referrence, which were obtained by the conventional hydration method (a method that an aqueous solution containing an active ingredient was employed in place of purified water when MLV was prepared as explained in Example 1). The relative ratio of the volume of aqueous solution containing an active ingredient to a unit weight of the lipid was kept in a prefixed condition (40 μl/mg lipid) throughout the tests. The mixture was warmed up at 50° C. for 2 minutes. The ingredients are quantitatively analyzed by a liquid chromtography where the condition is: Nucleocil $_{10}C_{18}$, 0.02M phosphate buffer (pH 7.4)/methanol=60/35, at 270 nm in case of cefalexin; 0.05M ammonium acetate/methanol=11/1, at 276 nm in case of latamoxef.

TABLE 3

| | Solvent | Uptake rate (%) | Captured Vol. (μl/mg) |
|---|---|---|---|
| | Freeze-dried sample of DPPC-MLV with cefalexin | | |
| 1 | Purified water | 37.0 | 14.4 |
| 2 | ½ Isotonic brine | 3.4 | 1.3 |
| | Freeze-dried sample of DPPC-MLV with latamoxef | | |
| 3 | Purified water | 34.4 | 13.8 |
| 4 | 0.05 M Phosphate buffer | 3.2 | 1.4 |
| 5 | Purified water (Hydration method, MLV) | 10.1 | 4.0 |

EXAMPLE 5

Two freeze-dried samples of MLV containing stearylamine (SA) or dicetyl phosphate (DCP), and DPPC were prepared at a mole ratio of 1/9 (DPPC/SA) or 1/9

(DPPC/DCP). To 15 mg each of the respective samples was added 0.2 ml of an aqueous solution (10 mg/ml) of latamoxef, and the mixtures were warmed up and kept at 50° C. for one minute to give liposomes. The respective uptake rates of thus obtained liposomes are 42.3% and 28.7%.

EXAMPLE 6

To 30 mg of the freeze-dried sample of MLV obtained in Example 1 was added 0.2 ml of an insulin solution (at 10 mg/ml, containing 0.01N hydrogen chloride). The mixture was ① warmed up and kept at 50° C. for 10 minutes, ② allowed to stand at room temperature. Or ③ after 30 mg of the sample was warmed up and kept at 50° C. for 10 minutes, insulin was added thereto. In the same manner as in Example 1, the uptake rates of insulin thereinto were measured and the data are summarized in Table 4.

TABLE 4

Freeze-dried sample of DPPC-MLV with insulin

| | Procedures employed | Uptake rate % |
|---|---|---|
| 1 | Warming up after addition of insulin | 60.5 |
| 2 | Allowed to stand at room temperature after addition of insulin | 3.0 |
| 3 | Adding insulin after the warming up | 1.6 |

EXAMPLE 7

A mixture of DL-DPPC (Sigma Chemical Co., type I-S, 200 mg) and dicetyl phosphate (1.5 mg) dissolved in chloroform was added to a 200 ml round-bottom flask and the solvent removed under reduced pressure by a rotary evaporator. To the thin dry lipid-film, 10 ml of distilled water was added, and gentle shaking was carried out at 50° C. The suspension was then freezed in a bath of dry ice-acetone and freeze-dried by a rotary vaccum pump.

To 10 mg of the freeze-dried product was added 0.4 ml of 5FU (2.5 mg/ml) aqueous solution which contained 10 μmol/ml CaCl$_2$ was added. After standing for 1 hour at room temperature, this system was warmed up for 5 minutes at 50° C. and 5FU-entrapped liposomes were prepared. The percentage of 5FU captured in liposomes was measured by a similar method to Example 1.

The results indicated that the percentage was 33% and the captured volume was 13.3 μl/mg lipid.

EXAMPLE 8

The liposome-water suspension prepared from L-DPPC (Avanti Polar Lipids, Inc., 100 mg) and stearylamine (0.37 mg) by a similar method to Example 7 was freeze-dried. To 10 mg of the freeze-dried product, 0.4 ml of 5FU (2.5 mg/ml) aqueous solution was added. After standing for 1 hour at room temperature, the system was warmed up for 5 minutes at 50° C. and 5FU-entrapped liposomes were prepared. The percentage of 5FU captured in liposomes was measured by a similar method to Example 1.

The results indicated that the percentage was 44% and the captured volume was 19 μl/mg lipid.

What is claimed is:

1. A process for preparing liposome compositions which comprises dispersing lyophilized multilamella vesicles or small unilamella vesicles in an aqueous medium in the presence of one or more clinically active ingredients at or over a temperature of the gel-phase/liquid crystal-phase transition.

2. A process claimed in claim 1, wherein said active ingredients are admixed with the vesicles before the lyophilization of said multilamella vesicles or small unilamella vesicles.

3. A process claimed in claim 1, wherein said active ingredients are admixed with said lyophilized multilamella vesicles or small unilamella vesicles and then dispersed in the aqueous medium.

4. A process claimed in claim 1, wherein the active ingredient is added in advance to the aqueous medium.

* * * * *